(12) United States Patent
Richardson et al.

(10) Patent No.: US 8,613,766 B2
(45) Date of Patent: Dec. 24, 2013

(54) MULTI-ELEMENT ACCOMMODATIVE INTRAOCULAR LENS

(75) Inventors: Gary A. Richardson, Dallas, TX (US); Josh Enin, Fontana, CA (US)

(73) Assignee: Bausch-Lomb Incorporated, Rochester, NY (US)

( * ) Notice: Subject to any disclaimer, the term of this patent is extended or adjusted under 35 U.S.C. 154(b) by 605 days.

(21) Appl. No.: 11/961,420

(22) Filed: Dec. 20, 2007

(65) Prior Publication Data

US 2008/0154364 A1 Jun. 26, 2008

Related U.S. Application Data

(60) Provisional application No. 60/871,567, filed on Dec. 22, 2006.

(51) Int. Cl.
*A61F 2/16* (2006.01)
(52) U.S. Cl.
USPC ........ 623/6.34; 623/6.37; 623/6.43; 623/6.49
(58) Field of Classification Search
USPC ............... 623/6.32, 6.34, 6.37, 6.38
See application file for complete search history.

(56) References Cited

U.S. PATENT DOCUMENTS

| | | | |
|---|---|---|---|
| 4,253,199 A | 3/1981 | Banko |
| 4,254,509 A | 3/1981 | Tennant |
| 4,271,841 A | 6/1981 | Friedman |
| 4,298,996 A | 11/1981 | Barnet |
| 4,373,218 A | 2/1983 | Schachar |
| 4,409,691 A | 10/1983 | Levy |
| 4,426,741 A | 1/1984 | Bittner |
| 4,463,458 A | 8/1984 | Seidner |
| 4,517,138 A | 5/1985 | Rawlings et al. |
| 4,517,139 A | 5/1985 | Rawlings et al. |
| 4,556,998 A | 12/1985 | Siepser |
| 4,575,373 A | 3/1986 | Johnson |
| 4,603,697 A | 8/1986 | Kamerling |
| 4,666,445 A | 5/1987 | Tillay |
| 4,680,149 A | 7/1987 | Rawlings et al. |
| 4,710,193 A | 12/1987 | Volk |
| 4,720,286 A | 1/1988 | Bailey et al. |
| 4,790,847 A | 12/1988 | Woods |
| 4,816,031 A | 3/1989 | Pfoff |

(Continued)

FOREIGN PATENT DOCUMENTS

| | | |
|---|---|---|
| DE | 19501444 A1 | 7/1996 |
| EP | 0162573 A2 | 11/1985 |

(Continued)

OTHER PUBLICATIONS

McLeod et al., "A dual optic accommodating foldable intraocular lens," Br J Ophthalmol, 2003, (vol. 87), (p. 1083-1085).

(Continued)

*Primary Examiner* — David H Willse
*Assistant Examiner* — Tiffany Shipmon
(74) *Attorney, Agent, or Firm* — Toan P. Vo

(57) ABSTRACT

A multi-element accommodating intraocular lens (AIOL) having a first anterior translation member and a first posterior translation member coupled together to form a first bias element. The first posterior translation member has a greater resistance to bending than the first anterior translation member. The first posterior translation member has a greater thickness than the first anterior translation member.

33 Claims, 5 Drawing Sheets

(56) References Cited

U.S. PATENT DOCUMENTS

| | | |
|---|---|---|
| 4,842,601 A | 6/1989 | Smith |
| 4,888,012 A | 12/1989 | Horn et al. |
| 4,892,543 A | 1/1990 | Turley |
| 4,902,293 A | 2/1990 | Feaster |
| 4,946,469 A | 8/1990 | Sarfarazi |
| 4,963,148 A | 10/1990 | Sulc et al. |
| 4,976,732 A | 12/1990 | Vorosmarthy |
| 4,989,605 A | 2/1991 | Rossen |
| 4,994,080 A | 2/1991 | Shepard |
| 4,994,082 A | 2/1991 | Richards et al. |
| 5,047,051 A | 9/1991 | Cumming |
| 5,076,683 A | 12/1991 | Glick |
| 5,108,429 A | 4/1992 | Wiley |
| 5,109,846 A | 5/1992 | Thomas |
| 5,152,789 A | 10/1992 | Willis |
| 5,173,723 A | 12/1992 | Volk |
| 5,201,762 A | 4/1993 | Hauber |
| 5,203,788 A | 4/1993 | Wiley |
| 5,275,623 A | 1/1994 | Sarfarazi |
| 5,275,624 A | 1/1994 | Hara et al. |
| 5,300,262 A | 4/1994 | Glick |
| 5,326,347 A | 7/1994 | Cumming |
| 5,360,438 A | 11/1994 | Fisher |
| 5,376,115 A | 12/1994 | Jansen |
| 5,391,202 A | 2/1995 | Lipshitz et al. |
| RE34,998 E | 7/1995 | Langerman |
| 5,476,514 A | 12/1995 | Cumming |
| 5,489,299 A | 2/1996 | Schachar |
| 5,489,302 A | 2/1996 | Skottun |
| 5,496,355 A | 3/1996 | Lipsky |
| 5,496,366 A | 3/1996 | Cumming |
| 5,593,436 A | 1/1997 | Langerman |
| 5,607,472 A | 3/1997 | Thompson |
| 5,620,720 A | 4/1997 | Glick et al. |
| 5,628,795 A | 5/1997 | Langerman |
| 5,674,282 A | 10/1997 | Cumming |
| 5,728,155 A | 3/1998 | Anello et al. |
| 5,769,890 A | 6/1998 | McDonald |
| 5,782,894 A | 7/1998 | Israel |
| 5,843,188 A | 12/1998 | McDonald |
| 6,013,101 A | 1/2000 | Israel |
| 6,051,024 A | 4/2000 | Cumming |
| 6,096,078 A | 8/2000 | McDonald |
| 6,117,171 A | 9/2000 | Skottun |
| 6,136,026 A | 10/2000 | Israel |
| 6,176,878 B1 | 1/2001 | Gwon et al. |
| 6,193,750 B1 | 2/2001 | Cumming |
| 6,197,059 B1 | 3/2001 | Cumming |
| 6,200,342 B1 | 3/2001 | Tassignon |
| 6,217,612 B1 | 4/2001 | Woods |
| 6,231,603 B1 | 5/2001 | Lang et al. |
| 6,299,641 B1 | 10/2001 | Woods |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,413,276 B1 | 7/2002 | Werblin |
| 6,423,094 B1 | 7/2002 | Sarfarazi |
| 6,428,573 B2 | 8/2002 | Barnett |
| 6,428,574 B1 | 8/2002 | Valunin et al. |
| 6,443,985 B1 | 9/2002 | Woods |
| 6,464,725 B2 | 10/2002 | Skotton |
| 6,478,821 B1 | 11/2002 | Laguette et al. |
| 6,485,516 B2 | 11/2002 | Boehm |
| 6,488,708 B2 | 12/2002 | Sarfarazi |
| 6,551,354 B1 | 4/2003 | Ghazizadeh et al. |
| 6,558,420 B2 | 5/2003 | Green |
| 6,616,691 B1 | 9/2003 | Tran |
| 6,616,692 B1 | 9/2003 | Glick et al. |
| 6,761,737 B2 | 7/2004 | Zadno-Azizi et al. |
| 6,764,511 B2 | 7/2004 | Zadno-Azizi et al. |
| 6,786,934 B2 | 9/2004 | Zadno-Azizi et al. |
| 6,818,158 B2 | 11/2004 | Pham et al. |
| 6,846,326 B2 | 1/2005 | Zadno-Azizi et al. |
| 6,858,040 B2 | 2/2005 | Nguyen et al. |
| 6,884,261 B2 | 4/2005 | Zadno-Azizi et al. |
| 6,899,732 B2 | 5/2005 | Zadno-Azizi et al. |
| 7,041,134 B2 | 5/2006 | Nguyen et al. |
| 7,087,080 B2 | 8/2006 | Zadno-Azizi et al. |
| 7,118,596 B2 | 10/2006 | Zadno-Azizi et al. |
| 2002/0116057 A1 | 8/2002 | Ting et al. |
| 2002/0161434 A1 | 10/2002 | Laguette et al. |
| 2003/0018384 A1* | 1/2003 | Valyunin et al. ............. 623/6.34 |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi et al. |
| 2003/0130732 A1* | 7/2003 | Sarfarazi ..................... 623/6.13 |
| 2004/0015236 A1 | 1/2004 | Sarfarazi |
| 2004/0160575 A1 | 8/2004 | Ayton et al. |
| 2004/0162612 A1 | 8/2004 | Portney et al. |
| 2005/0049700 A1 | 3/2005 | Zadno-Azizi et al. |
| 2005/0165410 A1 | 7/2005 | Zadno-Azizi et al. |
| 2005/0182419 A1 | 8/2005 | Tsai |
| 2005/0228401 A1 | 10/2005 | Zadno-Azizi et al. |
| 2005/0234547 A1 | 10/2005 | Nguyen et al. |
| 2005/0267575 A1 | 12/2005 | Nguyen et al. |
| 2006/0069431 A1* | 3/2006 | Graney et al. ................ 623/6.34 |
| 2006/0100703 A1 | 5/2006 | Evans et al. |
| 2006/0184244 A1 | 8/2006 | Nguyen et al. |
| 2007/0032866 A1 | 2/2007 | Portney |
| 2007/0260309 A1* | 11/2007 | Richardson .................. 623/6.34 |
| 2008/0312738 A1* | 12/2008 | Wanders ...................... 623/6.32 |

FOREIGN PATENT DOCUMENTS

| | | |
|---|---|---|
| EP | 0329981 A1 | 8/1989 |
| EP | 0336877 B1 | 10/1993 |
| EP | 0592813 A1 | 4/1994 |
| EP | 0328117 B1 | 12/1994 |
| EP | 0507292 B1 | 7/1997 |
| FR | 2784575 B1 | 4/2000 |
| JP | 02126847 A | 5/1990 |
| WO | WO 96/16780 A2 | 6/1996 |
| WO | WO 99/20206 A1 | 4/1999 |
| WO | WO 00/04849 A1 | 2/2000 |
| WO | WO 01/08607 A1 | 2/2001 |
| WO | WO 01/19289 A1 | 3/2001 |
| WO | WO 01/34067 A1 | 5/2001 |
| WO | WO 01/64136 A2 | 9/2001 |
| WO | WO 02/071983 A1 | 9/2002 |
| WO | WO 03/000154 A2 | 1/2003 |
| WO | WO 03/009051 A2 | 1/2003 |

OTHER PUBLICATIONS

Schachar, "Cause and treatment of presbyopia with a method for increasing the amplitude of accommodation," Ann Ophthalmol, 1992, (vol. 24), (p. 445-452).

Schachar et al., "Experimental support for Schachar's hypothesis of accommodation," Ann of Ophthalmol, Nov. 1993, (vol. 25), (Issue. 11), (p. 404-409).

Adler-Grinberg, "Questioning our classical understanding of accommodation and presbyopia," Amer J of Optometry & Physiol Optics, 1986, (vol. 63), (Issue. 7), (p. 571-580).

Schachar, "Zonular Function: A new hypothesis with clinical implications," Ann Ophthalmol, 1994, (vol. 26), (p. 36-38).

Koretz et al., "How the human eye focuses," Scientific American, Jul. 1988, (p. 92-99).

Hara et al., "Accommodative intraocular lens with spring action part I. Design and placement in an excised animal eye," Ophthal Surgery, Feb. 1990, (vol. 21), (Issue. 2), (p. 128-133).

Hara et al., "Accommodative intraocular lens with spring action—Part 2. Fixation in the living rabbit," Ophthal Surgery, Sep. 1992 (vol. 23), (Issue. 9), (p. 632-635).

Cimberle, "Three accommodative IOLs show high-quality surface on SEM," Ocular Surgery News, (p. 18-19), (Aug. 15, 2002).

* cited by examiner

MULTI-ELEMENT ACCOMMODATIVE INTRAOCULAR LENS

CROSS-REFERENCE

This application claims the benefit of Provisional Patent Application No. 60/871,567 filed Dec. 22, 2006.

FIELD OF INVENTION

The present invention relates to multi-element accommodative intraocular lenses (IOLs), and more particularly to multi-element accommodative intraocular lenses having a particular bias element construction.

BACKGROUND OF THE INVENTION

FIG. 1 illustrates a cross-sectional view of a human eye 10 having an anterior chamber 12 and a posterior chamber 14 separated by an iris 30. Within the posterior chamber 14 is a capsular bag 16 which holds the eye's natural crystalline lens 17. Light enters the eye by passing through cornea 18. The cornea and crystalline lens act together to direct and focus the light onto a retina 20. The retina is connected to optic nerve 22 which transmits images received by the retina to the brain for interpretation. Eye 10 has a visual axis VA.

In response to the sharpness of the image received by the retina, the brain operates to contract or relax ciliary muscle 26. Ciliary muscle 26 is disposed within ciliary body 28, and upon contraction of the ciliary muscle, the ciliary body is caused to move. To achieve near focus accommodation, the ciliary muscle is contracted thereby causing the ciliary body to relax tension on zonules 27 which permits the capsular bag and lens 17 to become more rounded. To achieve far focus (i.e., disaccommodation), the ciliary muscle is relaxed thereby increasing tension on zonules 27 which causes the capsular bag and lens 17 to become flatter.

In an eye where the natural crystalline lens has been damaged (e.g., clouded by cataracts), the natural lens is no longer able to properly focus and/or direct incoming light to the retina. As a result images become blurred. A well known surgical technique to remedy this situation involves removal of a damaged crystalline lens through a hole in the capsular bag known as a capsularhexis (also referred to simply as a rhexis). Subsequently, an artificial lens known as an intraocular lens (IOL) can be placed into the evacuated capsular bag through the rhexis.

Conventional IOLs are typically fixed-focus lenses. Such lenses are usually selected to have a power such that the patient has a fixed focus for distance vision, and the patient requires spectacles or contact lenses to permit near vision. In recent years extensive research has been carried out to develop IOLs having variable focus capability. Such IOLs are known as accommodating IOLs (AIOLS). The term "AIOLs" refers to both single-element and multi-element optical systems.

AIOLs permit a wearer to have accommodative vision. AIOLs are typically located in the posterior chamber (e.g., in the capsular bag) and provide variable focal power in accordance with tension or a lack of tension exerted on the capsular bag 16 as a result of contraction and relaxation of the ciliary muscle. FIG. 2 shows a cross section of an example of a two-element IOL 24 in capsular bag 16. IOL 24 comprises an anterior lens element 42 and a posterior lens element 44 that are connected to one another by bias elements 46. The bias elements permit lens elements 42 and 44 to translate relative to one another to achieve accommodation and disaccommodation. Further details of IOL 24 are given in U.S. Pat. No. 6,488,708 issued Dec. 3, 2002, to Sarfarazi Designs of AIOLs are commonly made using eye models that are based on assumptions about the mechanical properties of the capsular bag and how the AIOL will interact with the capsular bag to achieve a given amount of translation. Knowledge regarding the mechanical properties of the capsular bag and interaction with the AIOLs is evolving as clinical results from AIOL implantations are becoming available, and as computer modeling of the eye has advanced.

SUMMARY

To date some AIOL designs have been made assuming: (1) capsular bag shrinkage would be minimal due to the presence of the AIOL in the bag to resist the shrinkage, (2) the capsular bag will remain pliable such that substantial axial compression of the bias elements will occur due to pinching of the capsular bag on the bias elements (i.e., in the absence of the AIOL the empty capsule would be pulled flat in response to outward radial pressure provided by the zonules) (3) relative motion of the capsular bag and the bias element (e.g., sliding of the capsular bag over the AIOLs) would readily occur, thus facilitating pinching of the bias elements by the capsular bag. Also, to date, in at least some designs made using the above assumptions, the amount of translation of the anterior optic relative to the posterior element has been less than models employing the above assumptions have indicated should occur. It is becoming apparent that one or more of the above assumptions is at least partially incorrect.

Aspects of the present invention are directed to a multi-element AIOL having a posterior translation member of a bias element that is more rigid than in previous multi-element AIOL designs. In some embodiments, the posterior translation member of the bias element is more rigid than the anterior portion of the bias element. Current eye models based on new knowledge have indicated that such designs are better able to resist the effects of capsular bag shrinkage. And, in an accommodative state, such designs tension the capsular bag such that a radial force applied to capsular bag by the zonules more readily results in a pinching action on the AIOL bias elements thereby providing more translation of the lenses.

A first aspect of the invention is directed to a multi-element accommodating intraocular lens (AIOL) having an optical axis, comprising (A.) an anterior portion comprising (i.) an anterior optical element, and (ii.) a first anterior translation member coupled to the anterior optical element, and (iii.) a second anterior translation member coupled to the anterior optical element. The AIOL also comprises (B.) a posterior portion comprising (i.) a posterior optical element (ii.) a first posterior translation member coupled to the posterior optical element, and (iii.) a second posterior translation member coupled to the posterior optical element. The first anterior translation member and first posterior translation member are coupled together to form a first bias element, and the second anterior translation member and the second posterior translation member coupled together to form a second bias element. The first posterior translation member has a resistance to bending such that, at a point disposed at least 75% of the distance from the optical axis to the radially outermost location of the first bias element, a force of 0.1 mN causes less than 0.2 mm of displacement, when the lens is in an unstressed state.

According to some aspects, the first posterior translation member and the first anterior translation member are configured such that, at a point at least 75% of the distance from the optical axis to the radially outermost location of the first bias element, a force causes a displacement of the first anterior translation member that is at least 2.0 times the displacement of the first posterior translation member, when the lens is in an unstressed state.

According to some aspects, the first posterior translation member has a greater resistance to bending about the third attachment location than the first anterior translation member has about the first attachment location.

According to some aspects, the first posterior translation member has a greater thickness than the first anterior translation member.

According to some aspects, a plane perpendicular to the optical axis and passing through the radially outermost location of each bias element is closer to the first attachment location than the third attachment location.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 3:
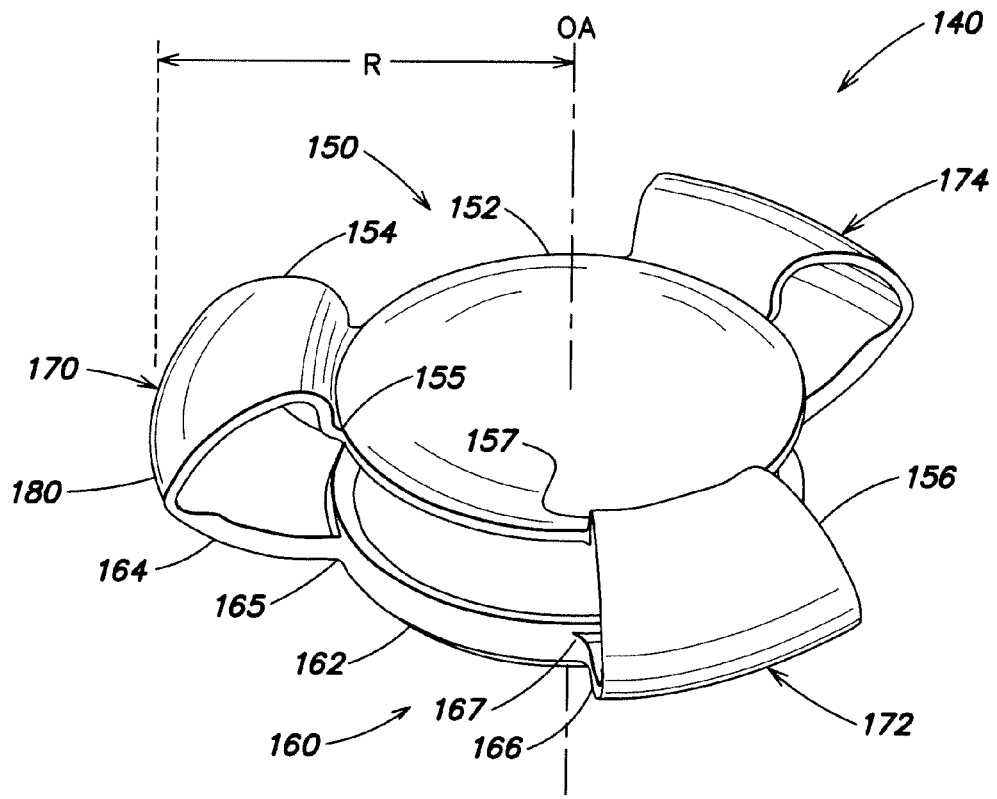
FIG. 3 is a perspective view of a two-element AIOL according to aspects of the present invention.

FIG. 3 is a perspective view of a multi-element AIOL 140 according to aspects of the present invention. AIOL 140 comprises an anterior portion 150 and a posterior portion 160.

The anterior portion comprises an anterior optical element 152, a first anterior translation member 154 coupled to the anterior optical element at a first attachment location 155, and a second anterior translation member 156 coupled to the anterior optical element at a second attachment location 157.

The posterior portion comprises a posterior optical element 162, a first posterior translation member 164 coupled to the posterior optical element at a third attachment location 165, and a second posterior translation member 166 coupled to the posterior optical element at a fourth attachment locations 167.

The first anterior translation member and first posterior translation member are connected together to form a first bias element 170, and the second anterior translation member and second posterior translation member connected together to form a second bias element 172. A third bias element 176 is configured and arranged similarly to bias elements 172 and 174. However, embodiments of an AIOL having two, four or more bias elements may be constructed.

Figure 5:
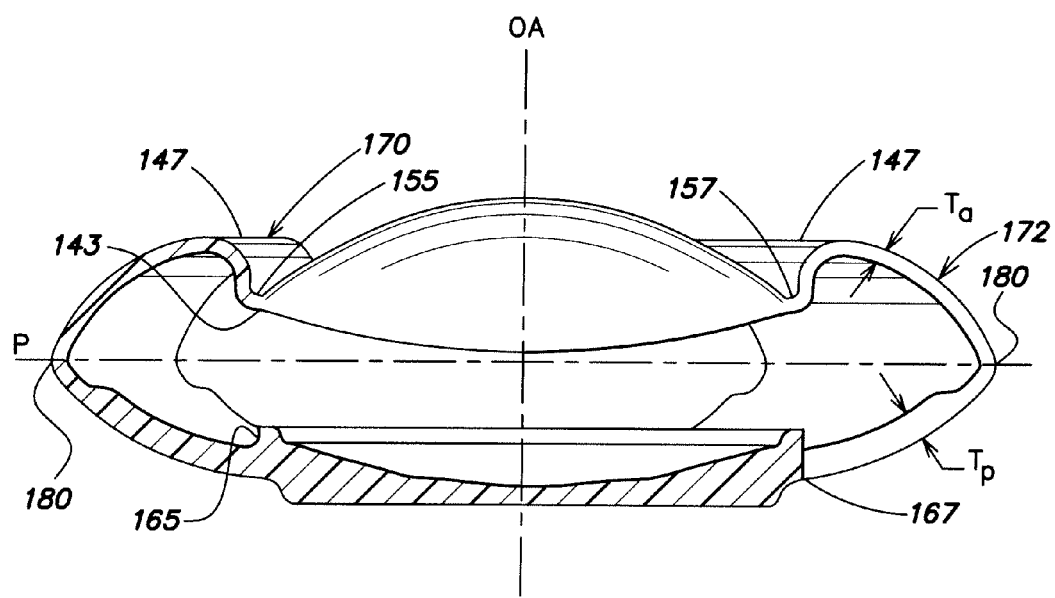
FIG. 5 is a cutaway, cross sectional, side view of the AIOL of FIG. 3.

Referring to FIG. 5, boundary between anterior portion 150 and posterior portion 160 on a given bias element (e.g., the boundary between an anterior translation member and a posterior translation member on the given bias element) is determined by extending a surface perpendicular to the optical axis of the AIOL and through the radially outermost location 180 of the given bias element. A radial outermost location is measured from optical axis OA of the AIOL to a given location.

Aspects of the present invention are directed to an AIOL having at least one bias element in which a posterior translation member has more resistance to bending than an anterior translation member. Aspects of the present invention are directed to an AIOL having at least one bias element in which a posterior translation member that is more rigid than in previous, AIOL designs. Eye models indicate that such AIOL designs at least partially resist the effects of capsular bag shrinkage and, in an accommodative state, tension the capsular bag to a greater degree than conventional designs, such that a radial force applied by the zonules to a capsular bag more readily results in a pinching action on the AIOL bias elements to achieve disaccommodation.

According to aspects of the present invention, first posterior translation member 164 has a greater resistance to bending about the third attachment location 165 than the first anterior translation member 154 has about the first attachment location 155. As a result, applying a force to the first posterior translation member at a selected radial distance R from the optical axis OA causes an angular deflection about the third attachment location that is less than the angular deflection caused by a force of the same magnitude applied to the first anterior translation member at the same radial distance R. It will be appreciated that although the angular deflection is measured about the attachment locations 155, 165, the bending may be greatest about a point that is proximate the attachment location. A point proximate the attachment location is typically within 1 mm from the edge of the optical element.

Any suitable technique to achieve a resistance to bending may be used. For example, in the illustrated embodiment, the posterior translation member has a greater thickness $T_P$ (shown in FIG. 5) than the anterior translation member thickness $T_A$. Any suitable differences in thicknesses of the posterior translation member and the anterior translation member may be used to attain a given difference in resistance to bending in the posterior translation member and in the anterior translation member as described above. For some silicone embodiments of an IOL, the posterior translation member has a thickness 0.3 mm while the anterior translation member has a thickness of 0.15 mm. In some embodiments, the posterior translation member has a thickness in the range 0.25 to 0.40 mm, and the anterior translation member has a thickness in the range 0.13 to 0.20 mm. Although the described embodiment is composed of Silicone, any suitable material may be used.

The posterior translation member will typically be thicker than the anterior translation member over a substantial portion of posterior translation member (e.g., greater than 50% of the length from the attachment location 165 to the radially outermost location 180, or greater than 75% of the length from the attachment location 165 to the radially outermost location 180). In the illustrated embodiment, the posterior translation members 164, 166 have greater thicknesses than the corresponding anterior translation members 154, 156 over approximately 90% of the length of the posterior translation member. In embodiments where an anterior translation member thickness varies over its length, the thickness of the posterior translation member is compared to the average anterior translation member thickness.

As illustrated in FIG. 3, a portion of the posterior translation member that is proximate the radially outermost location 180 has a reduced thickness relative to the remainder of the posterior translation member. Such a configuration facilitates bending of the biasing element to achieve a disaccommodated state.

Alternative examples of techniques for attaining a suitable resistance to bending include (1) selecting the width of the posterior translation member to be greater than the anterior translation member width, (2) selecting a stiffer material or combination of materials for the posterior translation member than the posterior translation members, (3) including a stiffening element inside or on an outside surface of the posterior translation member. A combination of the above techniques (including differences in thickness) may be used to achieve suitable resistance to bending. It is to be appreciated that although the resistances of the first anterior translation member and first posterior translation member of the first bias element have been discussed, any of the two or more bias elements (e.g., 172 and 174) of a given AIOL may be similarly constructed. It is typically appropriate that all of the bias elements of an AIOL are similarly constructed to one another; however, such a construction is not necessary.

Figure 4:
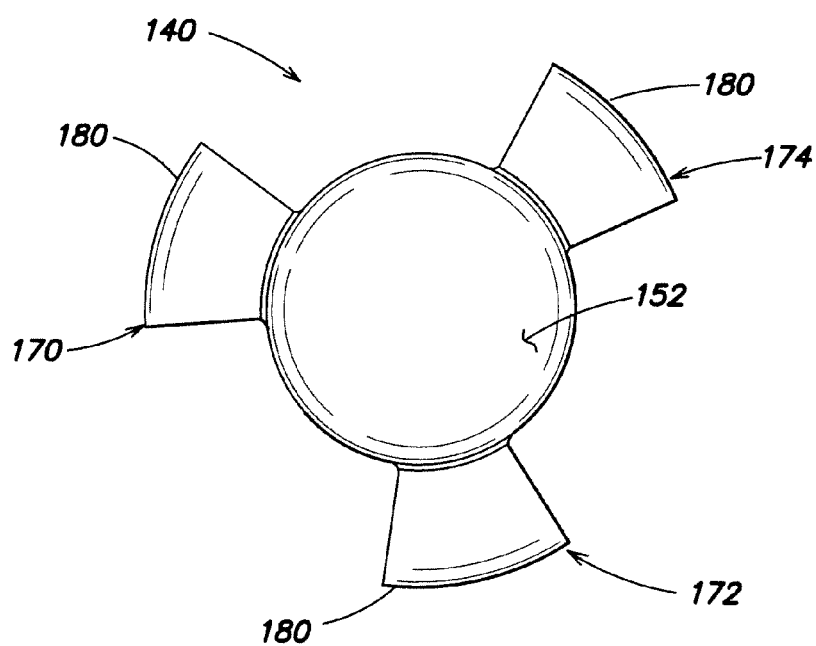
FIG. 4 is a plan view of the AIOL of FIG. 3.

Turning to FIG. 4, there is shown a plan view of AIOL 140. The bias elements 170, 172 and 174 of AIOL 140 are positioned around the peripheral edges of the optical elements of the AIOL. In the illustrated embodiment, the bias elements are equally spaced about the circumference of the optical elements; however, not all embodiments have such equal spacing. In a preferred embodiment, the bias elements subtend an angle of thirty to forty degrees, and extend outwardly approximately 4.65 mm from the optical axis (i.e., the overall diameter is approximately 9.3 mm in diameter), to approximate the typical internal diameter of the capsular bag of the human eye. Examples of suitable spring forces for an AIOL (as provided by all of the biasing element in conjunction) are given in U.S. patent application 60/798,548, titled ACCOMMODATIVE INTRAOCULAR LENS HAVING DEFINED AXIAL COMPRESSION CHARACTERISTICS, filed on May 8, 2006 by G. Richardson. Said application is hereby incorporated by reference in its entirety. The biasing elements are constructed such that optical axis OA align with the visual axis VA of a patient's eye when the AIOL is placed in the capsular bag of the eye.

As is apparent in FIG. 5, each bias element 170, 172, 174 has an anterior-most portion 147 that is disposed more anteriorly than an anterior side of edge 143 on the anterior optic. That is to say, the anterior optic is recessed relative to the bias elements. The anterior-most portion 147 of bias elements 170, 172, 174 is disposed approximately 0.5 to 0.8 mm more anteriorly than an anterior side of edge 143 of the anterior optic (as measured when the AIOL is fully hydrated and in a saline bath with substantially no stress applied to the lens).

In the illustrated embodiment of an AIOL, the bias elements 170, 172, 174 are angulated at the location where anterior translation member and the posterior translation member are connected together. However, in some embodiments, the bias elements 170, 172, 174 are curved at the connection locations of the anterior translation member and the posterior translation member. In such embodiments, there may be a continuous curvature along the bias element from the attachment location at the anterior optical element (e.g., first attachment location 155) to the attachment location at the posterior optical element (e.g., attachment location 165). The magnitude of the curvature may change along the length of the bias element.

In some embodiments, the first posterior translation member has a resistance to bending such that, at a point disposed at least 75% of the distance R from the optical axis to the radially outermost location 180 of the bias element, a force of 0.10 mN causes less than 0.2 mm of displacement of the point, when the lens is in an unstressed state. The term "unstressed state" means no force other than gravity and the 0.1 mN force are applied to the AIOL. In some embodiments, a force of 0.10 mN causes less than 0.1 mm of displacement of the point; and, in some embodiments, a force of 0.10 mN causes less than 0.065 mm of displacement of the point.

Modeling and displacement measurements of designs described herein were made using NSYS/Multiphysics FEA software package Version 10.0 with the following parameters:

Lens material elastic modulus: 1 MPa (approximately that of the NuSil Silicone material)

Element type: Solid92 (tetrahedral)

Solver: Nonlinear Static.

In some of the above embodiments, the point that is 75% of the distance R from the optical axis to the radially outermost location 180 is located at least 50% of the radial distance (i.e., in a direction perpendicular to the optical axis) from the anterior attachment location 155 to the radially outermost location 180 of the bias element; and in some of the above embodiments, the point that is 75% of the distance R from the optical axis to the radially outermost location 180 is located at least 75% of the radial distance (i.e., in a direction perpendicular to the optical axis) from the anterior attachment location 155 to the radially outermost location 180 of the bias element.

In some embodiments, the first posterior translation member and the first anterior translation member are configured such that, at a point at least 75% of the distance R from the optical axis to the radially outermost location 180 of the bias element, a force of 0.1 mN causes a displacement of the anterior translation member that is at least 2.0 times the displacement of the posterior translation member, when the lens is in an unstressed state. In some embodiments, the displacement of the anterior translation member is at least 3.0 times the displacement of the posterior translation member; and in some embodiments, the displacement of the anterior translation member is at least 3.5 times the displacement of the posterior translation member.

In some of the above embodiments, the point that is 75% of the distance R from the optical axis to the radially outermost location 180 is located at least 50% of the radial distance (i.e., in a direction perpendicular to the optical axis) from the anterior attachment location 155 to the radially outermost location 180 of the bias element; and in some of the above embodiments, the point that is 75% of the distance R from the optical axis to the radially outermost location 180 is located at least 75% of the radial distance (i.e., in a direction perpendicular to the optical axis) from the anterior attachment location 155 to the radially outermost location 180 of the bias element.

The optical power distribution of anterior optical element 152 and posterior optical element 162 may be selected to suit the needs of a particular patient. In some embodiments, the anterior optical element has a positive optical power and the posterior optical element has a negative optical power. In some embodiments, anterior optical element 152 is bi-convex, and the posterior optical element 162 is concavo-convex shape as depicted in FIG. 5. However, the posterior optical element and the anterior optical element may have surfaces of any suitable shape (e.g., concave or convex or planar) in order to achieve the desired visual result for a particular patient. In some embodiments, the accommodative effects of an AIOL are achieved with the anterior lens having optical power and the posterior element having no optical power.

As discussed above, in some embodiments, the anterior optical element and the posterior optical element are composed of a silicone material. However, any suitable material may be used. In some embodiments, optical elements are molded along with the bias elements to form an integrated AIOL device. Further details regarding manufacture of embodiments of an integrated lens are given in U.S. patent application Ser. No. 10/954,322 filed on Sep. 30, 2004, by Graney, et al. which is hereby incorporated by reference in its entirety.

Figure 6:
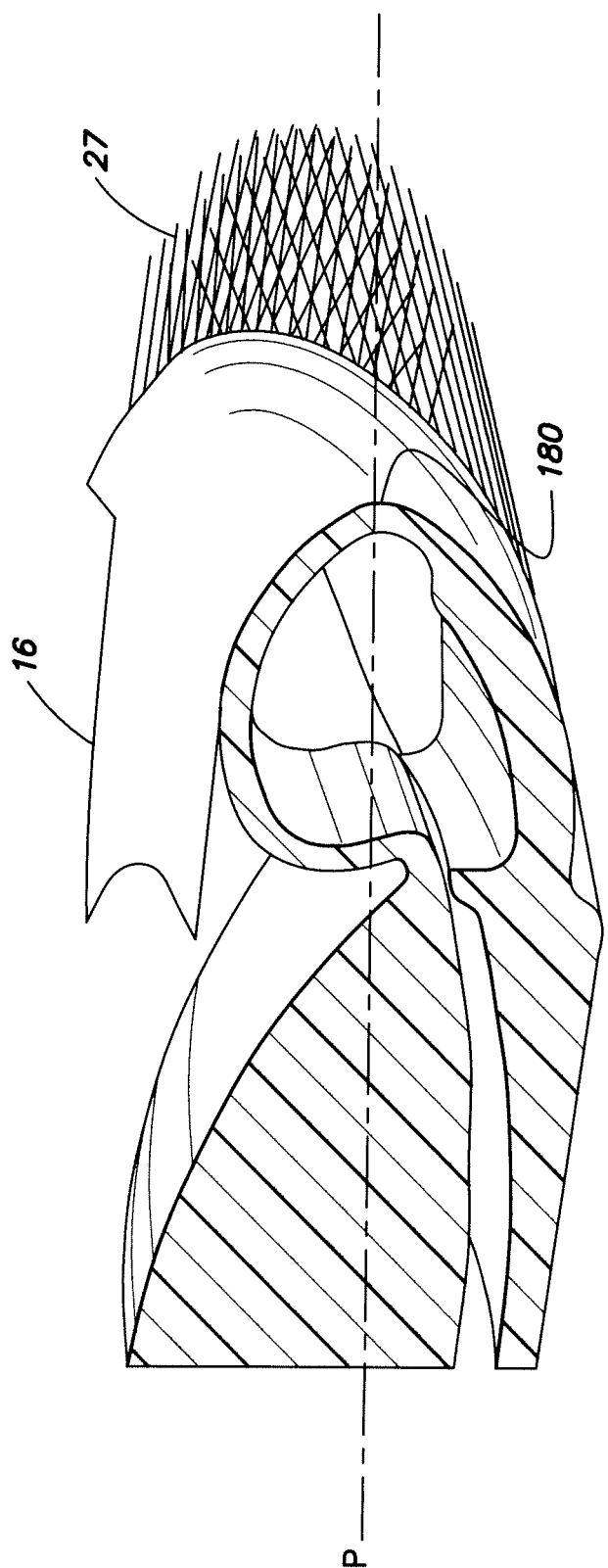
FIG. 6 is a side view of the AIOL of FIG. 3 in a disaccommodated state, in a capsular bag.

As is illustrated in FIG. 5, a plane P perpendicular to optical axis OA and passing through the radially outermost location 180 of each bias element is closer to anterior attachment locations 155 157 than posterior attachment location 165, 167. As illustrated in FIGS. 5 and 6, for the illustrated embodiment, the plane P is closer to the anterior attachment locations than the posterior attachment location, in both the accommodated and in the disaccommodated states. As illustrated in FIG. 6, the anterior attachment locations may be on the same side of plane P.

Figure 1:
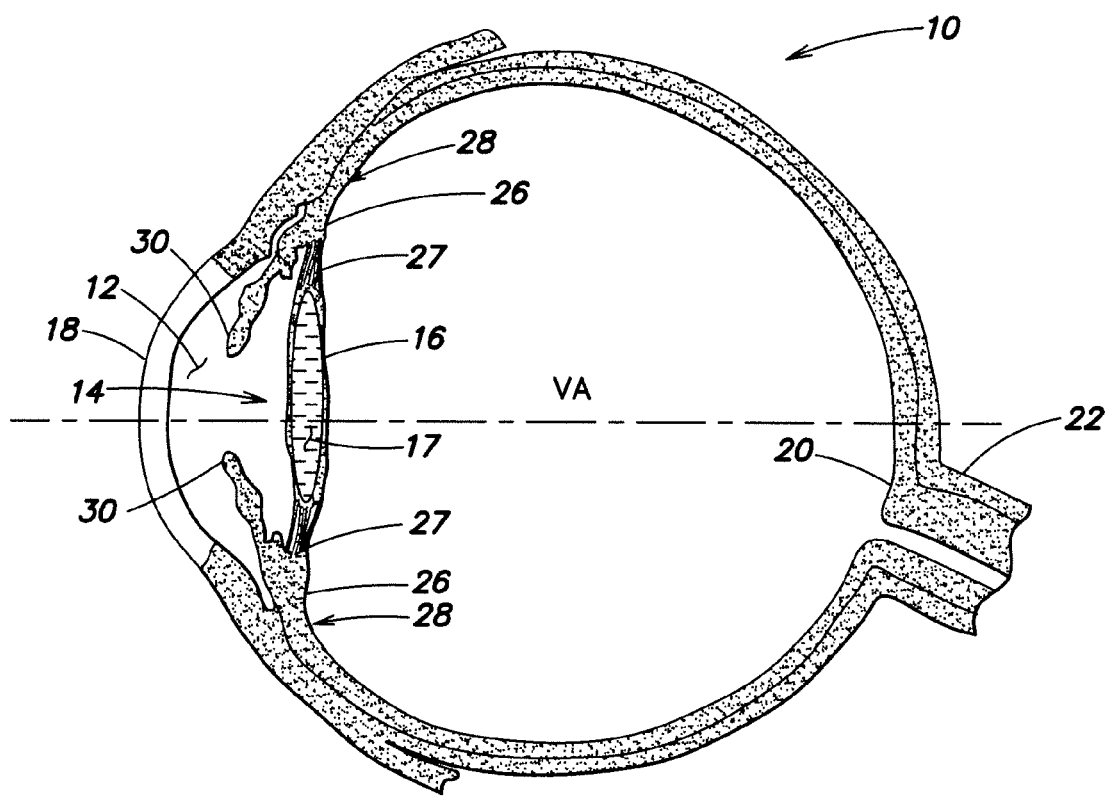
FIG. 1 illustrates a cross-sectional view of a human eye.
Figure 2:
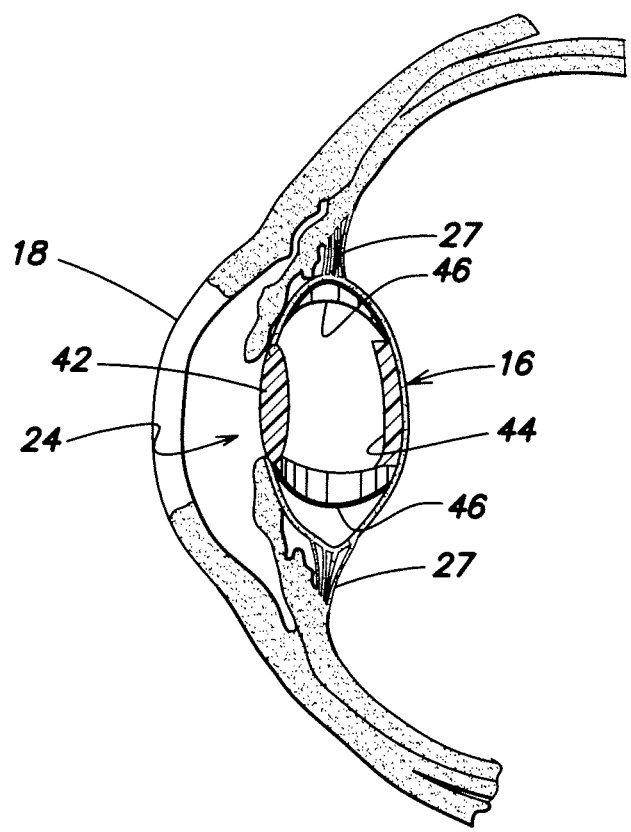
FIG. 2 shows a cross section of an example of a two-element AIOL in a capsular bag.

FIG. 6 is a schematic illustration of a portion of AIOL 140 positioned within a capsular bag 16 as described above with reference to FIG. 1. Zonules 27 extend peripherally about and are connected to the capsular bag 16. In FIG. 6, the eye is shown in a state where the ciliary muscle (not shown) is relaxed and retracted peripherally outwardly, the zonules 27 are tensioned outwardly pulling the equator of capsular bag 16. This position of the capsular bag causes the anterior optical element 152 and posterior optical element 162 to be positioned relatively near to one another to achieve distance (disaccommodative) vision.

Although not shown, it will be appreciated that, when the peripheral ciliary muscles are contracted, tension on the zonules 27 is lessened and the capsular bag assumes an accommodated state for near vision. In some embodiments, the subject AIOL is configured to permit anterior axial motion of the anterior lens with respect to the posterior lens of approximately 1.9 millimeters and a difference in optical power associated with the translation of approximately 4 diopters.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A multi-element accommodating intraocular lens (AIOL) having an optical axis, comprising:
  (A.) an anterior portion comprising—
   (i.) an anterior optical element, and
   (ii.) a first anterior translation member coupled to the anterior optical element, and
   (iii.) a second anterior translation member coupled to the anterior optical element, and
  (B.) a posterior portion comprising—
   (i.) a posterior optical element
   (ii.) a first posterior translation member coupled to the posterior optical element, and
   (iii.) a second posterior translation member coupled to the posterior optical element, and
  the first anterior translation member and first posterior translation member being integrally connected to form a first single piece bias element, and the second anterior translation member and the second posterior translation member integrally connected to form a second single piece bias element,
  wherein the first posterior translation member has a greater resistance to bending than the first anterior translation member, and the second posterior translation member has a greater resistance to bending than the second anterior translation member,
  the first posterior translation member having a resistance to bending such that, at a point disposed at least 75% of the distance from the optical axis to the radially outermost location of the first bias element, a force of 0.1 mN causes less than 0.2 mm of displacement, when the lens is in an unstressed state.

2. The AIOL of claim 1, wherein the force of 0.1 mN causes less than 0.1 mm of displacement.

3. The AIOL of claim 1, wherein the force of 0.1 mN causes less than 0.065 mm of displacement.

4. The AIOL of claim 1, further comprising a third biasing element coupled to the anterior optical element and the posterior element.

5. The AIOL of claim 4, further comprising a fourth biasing element coupled to the anterior optical element and the posterior element.

6. The AIOL of claim 1, wherein the first posterior translation member has a greater thickness than the first anterior translation member.

7. The AIOL of claim 1, wherein the first posterior translation member has a greater thickness than the first anterior translation member over at least 50% of the first posterior translation member length.

8. The AIOL of claim 1, wherein the anterior optical element is recessed relative to the first bias element and the second bias element.

9. The AIOL of claim 1, wherein the first anterior translation member and first posterior translation member are coupled together to form an angulated connection.

10. The AIOL of claim 1, wherein the first anterior translation member and first posterior translation member coupled together to form a curved connection.

11. The AIOL of claim 1, wherein the first anterior translation member is coupled to the anterior optical element at an anterior attachment location, and wherein the point is located at least 50% of the radial distance from the anterior attachment location to the radially outermost location.

12. The AIOL of claim 1, wherein the anterior optical element has a positive optical power and the posterior optical element has a negative optical power.

13. A multi-element accommodating intraocular lens (AIOL), comprising:
  (A.) an anterior portion comprising—
   (i.) an anterior optical element, and
   (ii.) a first anterior translation member coupled to the anterior optical element at a first attachment location, and
   (iii.) a second anterior translation member coupled to the anterior optical element at a second attachment location, and
  (B.) a posterior portion comprising—
   (i.) a posterior optical element
   (ii.) a first posterior translation member coupled to the posterior optical element at a third attachment location, and
   (iii.) a second posterior translation member coupled to the posterior optical element at a fourth attachment locations, and
  the first anterior translation member and first posterior translation member integrally connected to form a first single piece bias element, and the second anterior translation member and the second posterior translation member integrally connected to form a second single piece bias element, the first posterior translation member having a greater resistance to bending about the third attachment location than the first anterior translation member has about the first attachment location.

14. The AIOL of claim 13, further comprising a third biasing element coupled to the anterior optical element and the posterior element.

15. The AIOL of claim 14, further comprising a fourth biasing element coupled to the anterior optical element and the posterior element.

16. The AIOL of claim 13, wherein the first posterior translation member has a greater thickness than the first anterior translation member.

17. The AIOL of claim 13, wherein the first posterior translation member has a greater thickness than the first anterior translation member over at least 50% of the first posterior translation member length.

18. The AIOL of claim 13, wherein the anterior optical element is recessed relative to the first bias element and the second bias element.

19. The AIOL of claim 13, wherein the first anterior translation member and first posterior translation member are coupled together to form an angulated connection.

20. The AIOL of claim 13, wherein the first anterior translation member and first posterior translation member coupled together to form a curved connection.

21. The AIOL of claim 13, wherein the point is located at least 50% of the radial distance from the first attachment location to the radially outermost location of the first bias element.

22. The AIOL of claim 13, wherein the anterior optical element has a positive optical power and the posterior optical element has a negative optical power.

23. A multi-element accommodating intraocular lens (AIOL), comprising:
  (A.) an anterior portion comprising—
    (i.) an anterior optical element, and
    (ii.) a first anterior translation member coupled to the anterior optical element, and
    (iii.) a second anterior translation member coupled to the anterior optical element, and
  (B.) a posterior portion comprising—
    (i.) a posterior optical element
    (ii.) a first posterior translation member coupled to the posterior optical element, and
    (iii.) a second posterior translation member coupled to the posterior optical element, and
  the first anterior translation member and first posterior translation member integrally connected to form a first single piece bias element, and the second anterior translation member and the second posterior translation member integrally connected to form a second single piece bias element,
  the first posterior translation member having a greater thickness than the first anterior translation member.

24. The AIOL of claim 23, further comprising a third biasing element coupled to the anterior optical element and the posterior element.

25. The AIOL of claim 24, further comprising a fourth biasing element coupled to the anterior optical element and the posterior element.

26. The AIOL of claim 23, wherein the first posterior translation member has a greater thickness than the first anterior translation member over at least 50% of the first posterior translation member length.

27. The AIOL of claim 23, wherein the anterior optical element is recessed relative to the first bias element and the second bias element.

28. The AIOL of claim 23, wherein the first anterior translation member and first posterior translation member are coupled together to form an angulated connection.

29. The AIOL of claim 23, wherein the first anterior translation member and first posterior translation member coupled together to form a curved connection.

30. The AIOL of claim 23, wherein the anterior optical element has a positive optical power and the posterior optical element has a negative optical power.

31. A multi-element accommodating intraocular lens (AIOL) having an optical axis, comprising:
  (A.) an anterior portion comprising—
    (i.) an anterior optical element, and
    (ii.) a first anterior translation member coupled to the anterior optical element at a first attachment location, and
    (iii.) a second anterior translation member coupled to the anterior optical element at a second attachment location, and
  (B.) a posterior portion comprising—
    (i.) a posterior optical element
    (ii.) a first posterior translation member coupled to the posterior optical element at a third attachment location, and
    (iii.) a second posterior translation member coupled to the posterior optical element at a fourth attachment location, and
  the first anterior translation member and first posterior translation member coupled together to form a first bias element, and the second anterior translation member and the second posterior translation member coupled together to form a second bias element, and
  wherein the first posterior translation member has a greater resistance to bending than the first anterior translation member, and the second posterior translation member has a greater resistance to bending than the second anterior translation member,
  a plane perpendicular to the optical axis and passing through the radially outermost location of each bias element is closer to the first attachment location than the third attachment location.

32. The AIOL of claim 31, wherein the plane is closer to first attachment location than the third attachment location, when the AIOL is in an accommodative state.

33. The AIOL of claim 31, wherein the plane is closer to first attachment location than the third attachment location, when the AIOL is in an disaccommodative state.

* * * * *